(12) United States Patent
Straessler

(10) Patent No.: US 7,737,308 B1
(45) Date of Patent: Jun. 15, 2010

(54) METHODS FOR NITRATING COMPOUNDS

(75) Inventor: Nicholas A. Straessler, Plain City, UT (US)

(73) Assignee: Alliant Techsystems Inc., Minneapolis, MN (US)

( * ) Notice: Subject to any disclaimer, the term of this patent is extended or adjusted under 35 U.S.C. 154(b) by 0 days.

(21) Appl. No.: 12/484,960

(22) Filed: Jun. 15, 2009

(51) Int. Cl.
*C07C 205/00* (2006.01)
(52) U.S. Cl. ...................... 568/706; 568/710
(58) Field of Classification Search ............. 568/706, 568/710
See application file for complete search history.

(56) References Cited

U.S. PATENT DOCUMENTS

| | | | | |
|---|---|---|---|---|
| 1,380,186 A * | 5/1921 | Brewster | .................... | 568/710 |
| 1,396,001 A | 11/1921 | MacDonald | | |
| 2,246,963 A * | 6/1941 | Wilkinson | .................. | 568/710 |
| 3,278,604 A | 10/1966 | Hoffman et al. | | |
| 3,394,183 A | 7/1968 | Dacons et al. | | |
| 3,933,926 A | 1/1976 | Salter et al. | | |
| 3,954,852 A | 5/1976 | Shen et al. | | |
| 4,032,377 A | 6/1977 | Benziger | | |
| 4,232,175 A | 11/1980 | Smith et al. | | |
| 4,434,304 A | 2/1984 | DeFusco, Jr. et al. | | |
| 4,745,232 A * | 5/1988 | Schmitt et al. | .............. | 568/712 |
| 4,952,733 A | 8/1990 | Ott et al. | | |
| 4,997,987 A | 3/1991 | Ott et al. | | |
| 5,371,291 A * | 12/1994 | Nader | ........................ | 564/418 |
| 5,569,783 A | 10/1996 | Mitchell et al. | | |
| 5,633,406 A | 5/1997 | Mitchell et al. | | |
| 6,069,277 A | 5/2000 | Mitchell et al. | | |
| 7,057,072 B2 | 6/2006 | Mitchell et al. | | |
| 7,057,073 B2 | 6/2006 | Mitchell et al. | | |

FOREIGN PATENT DOCUMENTS

| | | |
|---|---|---|
| GB | 2355715 A | 5/2001 |
| GB | 2355714 | 3/2004 |
| WO | 9419310 A1 | 9/1994 |

OTHER PUBLICATIONS

Agrawal, J.P., et al., Organic Chemistry of Explosives, pp. 142-143, © 2007, John Wiley & Sons Ltd., West Sussex, England.
Bellamy, A., et al., "Nitration of 1,3,5-trimethoxybenzene," J. Chem. Research (S), pp. 412-413, 2002.
Bellamy, A., et al., "Nitration of 1,3,5-trimethoxybenzene," J. Chem. Research (M), pp. 0919-0930, 2002.
Bellamy, Anthony J., et al., "A New Synthetic Route to 1,3,5-Triamino-2,4,6-Trinitrobenzene (TATB)," Propellants, Explosives, Pyrotechnics, vol. 27, pp. 49-58, 2002.
Bellamy, Anthony J., et al., "Synthesis of Ammonium Diaminopicrate (ADAP), a New Secondary Explosive," Propellants, Explosive, Pyrotechnics, vol. 27, pp. 59-61, 2002.
Bose, P.C., et al., "Occurrence of Dehydrorotenone in Derris uliginosa Benth," Indian J. Chem., vol. 14B, pp. 1012-1013, Dec. 1976.
DeFusco, A.A., et al., "An Improved Preparation of Trinitrophloroglucinol," Organic Preparations and Procedures Int., vol. 14, No. 6, pp. 393-424, 1982.
Dobratz, Brigitta M., "The Insensitive High Explosive Triaminotrinitrobenzene (TATB): Development and Characterization—1988 to 1994," Los Alamos Nat'l. Lab., LA-13014-H, History, UC-741, 151 pages, Aug. 1995.
Dove, Michael F.A., et al., "Vanadium(v) oxytrinitrate, VO(NO3)3. A powerful reagent for the nitration of aromatic compounds at room temperature under non-acidic conditions," J. Chem. Soc., Perkin Trans. 1, pp. 1589-1590, 1998.
Hoffman, D. Mark, et al., "Comparison of New and Legacy TATBs," Journal of Energetic Materials, vol. 26, pp. 139-162, 2008.
Hofmann, K.A., et al., "Verbindungen von Kobaltnitriten mit p-Toluidin, Diazoaminotoluol, Hydrazin und Nitrosohydrazin," Miteilung a. d. Chem. Laborat. D. Kgl. Akad. D. Wissenschafter zu Munchen, Eingengangen am 14, Aug. 1908, pp. 3084-3090.
Maiti, A., et al., "Solvent screening for a hard-to-dissolve molecular crystal," Physical Chemistry Chemical Physics, vol. 10, pp. 5050-5056, 2008.
Majumdar, M.P., et al., "Nitration of Organic Compounds with Urea Nitrate-Sulphuric Acid," Indian J. Chem., vol. 14B, pp. 1012-1013, Dec. 1976.
Mehilal, et al., "Studies on 2,4,6-trinitrophloroglucinol (TNPG)—A novel flash sensitizer," Indian Journal of Engineering & Materials Sciences, vol. 11, pp. 59-62, Feb. 2004.
Mellor, John M., et al., "Improved Nitrations Using Metal Nitrate—Sulfuric Acid Systems," Tetrahedron, vol. 56, pp. 8019-8024, 2000.
Mitchell, Alexander R., et al., "A New Synthesis of TATB Using Inexpensive Starting Materials and Mild Reaction Conditions," prepared for submittal to the 27th International Annual Conference of ICT, Jun. 25-28, 1996, Karlsruhe, Federal Republic of Germany, 14 pages, Apr. 1996.
Olah, George A., et al., "New Synthetic Reagents and Reactions," Aldrichimica Acta, vol. 12, No. 3, pp. 43-49, 1979.
Olah, George A., et al., Nitration Methods and Mechanisms, © 1989 VCH Publishers, Inc., New York, NY, p. 29.
Ott, D.G., et al., "Preparation of 1,3,5-Triamino-2,4,6-Trinitrobenzene from 3,4-Dichloroanisole," Journal of Energetic Materials, vol. 5, pp. 343-354, 1987.
Schedule of 2008 GRC on Energetic Materials, 5 pages.
Schmidt, Robert D., et al., "New Synthesis of TATB. Process Development Studies," prepared for submittal to the JOWOG 9 (Joint Working Group 9), Aldermaston, England, Jun. 22-26, 1998, 14 pages, May 1998.
Smith, Bengt, "The Reaction between Phenols and Orthoesters. A New Synthesis of Aryl Alkyl Ethers," Acta Chem. Scand., vol. 10, No. 6, pp. 1006-1010, 1956.

(Continued)

*Primary Examiner*—Sikarl A Witherspoon
(74) *Attorney, Agent, or Firm*—TraskBritt

(57) ABSTRACT

Methods of nitrating compounds, such as phloroglucinol or a methoxy derivative thereof, are disclosed. For example, a reaction mixture may be formed by combining sulfuric acid and at least one nitrate salt. A nitratable aromatic compound, such as phloroglucinol or a methoxy derivative thereof, may then be exposed to the reaction mixture to nitrate the phloroglucinol or methoxy derivative thereof.

17 Claims, 4 Drawing Sheets

OTHER PUBLICATIONS

U.S. Appl. No. 11/744,986, filed May 7, 2007, entitled, "Methods of Producing 1,3,5-Triamino-2,4,6-Trinitrobenzene."

Waller, Francis J., et al., "Lanthanide(III) and Group IV metal triflate catalysed electrophilic nitration: 'nitrate capture' and the role of the metal centre," J. Chem. Soc., Perkin Trans. 1, pp. 867-871, 1999.

Zolfigol, Mohammad Ali, et al., "Nitration of Aromatic Compounds on Silica Sulfuric Acid," Bull. Korean Chem. Soc., vol. 25, No. 9, pp. 1414-1416, 2004.

Zolfigol, Mohammad Ali, et al., "Silica Sulfuric Acid/ NaNO2 as a Novel Heterogeneous System for the Nitration of Phenols under Mild Conditions," Molecules, vol. 7, pp. 734-742, 2002.

U.S. Appl. No. 12/484,917, filed Jun. 15, 2009, entitled, "Methods for the Production of 1,3,5-Triamino-2,4,6-Trinitrobenzene".

U.S. Appl. No. 12/484,985, filed Jun. 15, 2009, entitled, "Methods of Producing 1,3,5-Triamino-2,4,6-Trinitrobenzene".

http://en.wikipedia.org/wiki/Room_temperature, Room Temperature, last visited Dec. 11, 2009.

* cited by examiner

METHODS FOR NITRATING COMPOUNDS

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Contract No. W912HQ-07-C-0018 awarded by the Strategic Environmental Research and Development Program (SERDP).

CROSS-REFERENCE TO RELATED APPLICATIONS

This application is related to co-pending U.S. patent application Ser. No. 11/744,986 to Velarde et al., entitled "METHODS OF PRODUCING 1,3,5-TRIAMINO-2,4,6-TRINITROBENZENE," filed on May 7, 2007. This application is also related to co-pending U.S. patent application Ser. Nos. 12/484,985 entitled "METHODS OF PRODUCING 1,3,5-TRIAMINO-2,4,6-TRINITROBENZENE," and 12/484,917 entitled "METHODS FOR THE PRODUCTION OF 1,3,5-TRIAMINO-2,4,6-TRINITROBENZENE," each of which was filed on Jun. 15, 2009, and assigned to the Assignee of the present application. The disclosure of each of the three above-mentioned applications is incorporated by reference herein in its entirety.

TECHNICAL FIELD

The present invention, in various embodiments, relates to methods of nitrating aromatic compounds and, more particularly, to methods of nitrating phloroglucinol and derivatives thereof to produce 1,3,5-triamino-2,4,6-trinitrobenzene precursors.

BACKGROUND

Nitration reactions are important chemical transformations employed in the production of many energetic materials. For example, a conventional method for manufacturing the insensitive explosive 1,3,5-triamino-2,4,6-trinitrobenzene (TATB) uses 1,3,5-tricholorobenzene (TCB) as a starting material in a two stage process that includes: (1) a nitration reaction; and (2) an amination reaction. However, due to the environmental hazards associated with halogenated aromatics, phenolic compounds are, when applicable, substituted as starting materials in these types of syntheses. Unfortunately, nitration of even moderately activated aromatics may result in vigorously exothermic reactions that require strict temperature control by way of substantial cooling. Such processing requirements may be difficult to maintain, particularly in terms of scaling-up nitration reactions to production level quantities.

Conventional methods of producing nitro phenols, therefore, avoid the direct nitration of the phenol and employ processes that initially form an intermediate compound that may then be nitrated. Phenol, for instance, is first sulfonated to form a mixture of phenolsulfonic acids that are then nitrated to produce picric acid (2,4,6-trinitrophenol). Resorcinol is reacted similarly to produce styphnic acid (2,4,6-trinitroresorcinol), and phloroglucinol (1,3,5-trihydroxybenzene) is first converted to a triacetoxy derivative, which is nitrated and then hydrolyzed to produce trinitrophloroglucinol. Another method of preparing nitrophenols is by hydrolysis of an appropriate halogenated derivative. For example, 2,4-dinitrochlorobenzene may be hydrolyzed by aqueous alkali to form 2,4-dinitrophenol, which may be subsequently nitrated to picric acid. Similarly, 1,3,5-tribromo-2,4,6-trinitrobenzene may be hydrolyzed to produce trinitrophloroglucinol. These processes do not offer significant advantages in time and labor, and the presence of halides is still problematic. Furthermore, the action of the alkali on the nitro groups may introduce unwanted decomposition products that may result in impure products.

Bellamy et al., *Propellants, Explosives, Pyrotechnics*, 27: 49-58 (2002), disclose a three-stage route to manufacturing TATB using 1,3,5-trihydroxybenzene as a starting material. The 1,3,5-trihydroxybenzene is nitrated using dinitrogen pentoxide ($N_2O_5$) in sulfuric acid ($H_2SO_4$), or a mixed acid nitration of the triacetate analog.

Bellamy et al., *J. Chem. Research*, 2002(9): 412-413 (2002), disclose a process for nitrating 1,3,5-trimethoxybenzene using dinitrogen pentoxide dissolved in an organic solvent, such as dichloromethane or acetonitrile, in the presence of nitric acid or sulfuric acid. In all experiments where an amount of dinitrogen pentoxide sufficient to convert 1,3,5-trimethoxybenzene to the tri-nitro derivative was used, the product yield was 22-65%. The highest conversion of 1,3,5-trimethoxybenzene into 1,3,5-trimethoxy-2,4,6-trinitrobenzene was achieved when sulfuric acid was present. However, Bellamy et al. observed that too much sulfuric acid caused the yield to be drastically reduced. Additionally, the nitration process using nitric acid was observed to cause significant side-reactions.

DeFusco et al., *Organic Preparations and Procedures International*, 14(6): 393-424 (1982), disclose a preparation of trinitrophloroglucinol performed by adding a nitric acid-sulfuric acid mixture to a phloroglucinol-sulfuric acid mixture. The preparation produced yields of up to 70%.

M. P. Majumdar and N. A. Kudav, *Ind. J. Chem.*, 14B: 1012-1013 (1976), disclose nitration of aromatic compounds, such as anisole, diphenyloxide, methyl benzoate, and acetophenone, with urea nitrate-sulfuric acid. A mixture of the aromatic compound and concentrated sulfuric acid is treated with urea nitrate at 0° C. to 10° C. while stirring for one hour to achieve nitration.

*Organic Chemistry of Explosives*, by J. P. Agrawal and R. D. Hodgson, pp. 142-143, discloses a nitration process using a solution of potassium nitrate in sulfuric acid to nitrate o- or p-acetanilide to form picramide. Metal nitrates are also disclosed for use with Lewis acids for aromatic nitration, as well as using alkyl nitrates in the presence of sulfuric acid and Lewis acids, such as $SnCl_4$, $AlCl_3$, or $BF_3$.

U.S. Pat. No. 4,032,377 to Theodore M. Benziger discloses a method for producing TATB from TCB using a nitration process, followed by an amination process. The TCB is nitrated using a mixture of oleum and sodium nitrate at 150° C. for 4 hours to form 1,3,5-trichloro-2,4,6-trinitrobenzene, which is, in turn, aminated using ammonia in toluene at 150° C. This process relies on extreme reaction conditions that necessitate high temperatures over relatively long periods of time. Additionally, environmental concerns have arisen over the release and use of halogenated aromatic compounds, such as TCB, in the manufacture of TATB, and subsequent disposal of such compounds. Halogenated aromatics, and other halogen-containing compounds, have been found to be highly toxic, potential carcinogens. Accordingly, unconverted halogenated compounds and halogen containing side-products must be suitably disposed of to prevent pollution which, in turn, results in increased manufacturing costs.

U.S. Pat. No. 4,952,733 to Ott and Benziger discloses a method of preparing TATB from nitration of 3,5-dichloroanisole. The reaction sequence consists of a two step process involving a nitration reaction, followed by an amination reaction. The nitration reaction is performed by adding 3,5-dichloroanisole to a mixture of nitric acid and sulfuric acid at a temperature of 100° C.

BRIEF SUMMARY OF THE INVENTION

One embodiment of the present invention includes methods of nitrating a compound. The method comprises combining at least one nitrate salt and a sulfuric acid solution to form a reaction mixture and exposing phloroglucinol or a methoxy derivative thereof to the reaction mixture to nitrate the phloroglucinol or methoxy derivative thereof. The at least one nitrate salt may be, for example, sodium nitrate, potassium nitrate, ammonium nitrate, calcium nitrate or magnesium nitrate. The at least one nitrate salt may be combined with a sulfuric acid solution that includes about 90% by weight to about 100% by weight sulfuric acid to form the reaction mixture. The phloroglucinol or a methoxy derivative exposed to the reaction mixture may include, for example, phloroglucinol, 5-methoxyresorcinol, 3,5-dimethoxyphenol, and 1,3,5-trimethoxybenzene.

Another embodiment of the present invention includes a method of nitrating a compound that includes reacting phloroglucinol or a methoxy derivative thereof with a reaction mixture comprising sulfuric acid and at least one nitrate salt to nitrate the phloroglucinol or the methoxy derivative thereof. For example, three molar equivalents of the at least one nitrate salt may be reacted with the phloroglucinol or the methoxy derivative thereof. The method may be used to produce a mononitrated, dinitrated, or trinitrated compound of phloroglucinol or methoxy derivative thereof. As a non-limiting example, the at least one nitrate salt may be added to the sulfuric acid at a temperature in a range of from about 0° C. to about 10° C. and then mixed with the phloroglucinol or the methoxy derivative thereof at a temperature in a range of from about 0° C. to about 10° C. to form a slurry or homogeneous solution. The mixture may be stirred, for example, at a temperature in a range of from about 0° C. to about 27° C. to nitrate the phloroglucinol or the methoxy derivative thereof.

BRIEF DESCRIPTION OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

DETAILED DESCRIPTION

Figure 1:
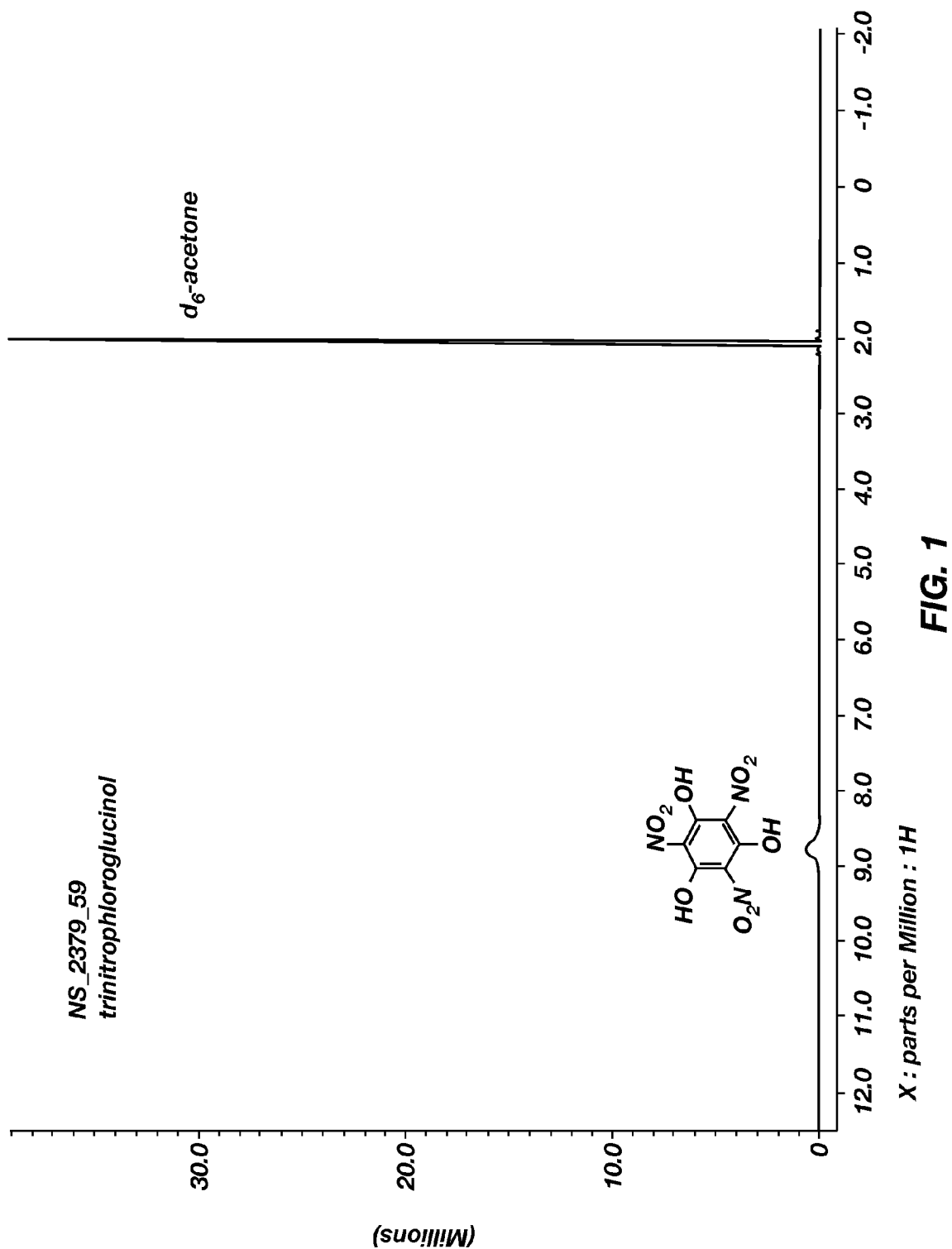
FIGS. 1-4 are proton nuclear magnetic resonance spectra for compounds formed by the processes described in Examples 1-4, respectively.

As used herein, the terms "comprising," "including," "containing," "characterized by," and grammatical equivalents thereof are inclusive or open-ended terms that do not exclude additional, unrecited elements or method steps, but also include the more restrictive terms "consisting of" and "consisting essentially of" and grammatical equivalents thereof. As used herein, the term "may" with respect to a material, structure, feature, or method act indicates that such is contemplated for use in implementation of an embodiment of the invention and such term is used in preference to the more restrictive term "is" so as to avoid any implication that other compatible materials, structures, features, and methods usable in combination therewith should, or must be, excluded.

A method of nitrating a nitratable aromatic compound is described. As used herein, the term "nitratable aromatic compound" means and includes an aromatic compound having at least one hydrogen moiety which may be substituted with a nitro functional group (—$NO_2$). For example, the nitratable aromatic compound may include an arylbenzene, an alkylbenzene, a phenylamine, an aromatic ether, or a phenolic compound. The nitratable aromatic compound may be, for example, biphenyl, toluene, aniline, or anisole. The term "phenolic compound," as used herein, means and includes a compound having at least one hydroxyl group bound to a benzene ring. The phenolic compound may include an alkyl phenol, such as a cresol, a phenol ether, or an alkenyl phenol. The phenolic compound may include, but is not limited to, phloroglucinol (1,3,5-trihydroxybenzene) or a methoxy derivative thereof, such as 5-methoxyresorcinol, 3,5-dimethoxyphenol, or 1,3,5-trimethoxybenzene. Phloroglucinol and the methoxy derivatives of phloroglucinol (5-methoxyresorcinol, 3,5-dimethoxyphenol and 1,3,5-trimethoxybenzene) are commercially available, such as from Sigma-Aldrich Co. (St. Louis, Mo.).

The nitratable aromatic compound may be directly nitrated using a mixture of a nitrate salt and sulfuric acid ($H_2SO_4$). The term "directly nitrated" means and includes nitrating the nitratable aromatic compound in a single reaction, without forming an intermediate compound that is then subsequently nitrated. The nitration reaction produces a nitrated aromatic compound. The nitrate salt may be sodium nitrate ($NaNO_3$), potassium nitrate ($KNO_3$), ammonium nitrate ($NH_4NO_3$), calcium nitrate ($Ca(NO_3)_2$), magnesium nitrate ($Mg(NO_3)_2$) or combinations thereof. The nitrate salts and the sulfuric acid are commercially available from various sources, such as from Sigma-Aldrich Co. (St. Louis, Mo.). An exemplary reaction scheme for producing the nitrated aromatic compound is shown below:

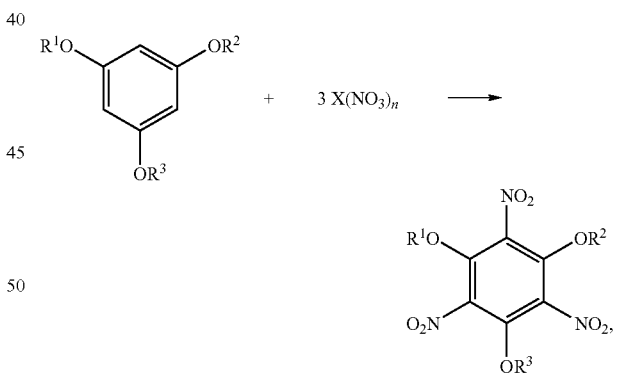

where $R^1$, $R^2$, and $R^3$ are each independently H or an alkyl group, and X is $Na^+$, $K^+$, $NH_4^+$, $Ca^{2+}$, or $Mg^{2+}$. While specific examples below describe using ammonium nitrate as the nitrate salt, other nitrate salts may be used. In addition, mixtures of nitrate salts may be used. While the reaction scheme above illustrates that three molar equivalents of the nitrate salt may be used relative to the nitratable aromatic compound, one or two molar equivalents of the nitrate salt may be used to produce a mono- or di-nitrated aromatic compound.

By way of non-limiting example, phloroglucinol, or a methoxy derivative thereof, may be nitrated to form trinitrophloroglucinol or a methoxy derivative thereof. Reaction schemes for producing trinitrophloroglucinol (1,3,5-trihydroxy-2,4,6-trinitrobenzene) from phloroglucinol, 5-methoxystyphnic acid (5-methoxy-2,4,6,-trinitroresorcinol) from 5-methoxyresorcinol, 3,5-dimethoxypicric acid (3,5-dimethoxy-2,4,6-trinitrophenol) from 3,5-dimethoxyphenol, and 1,3,5-trimethoxy-2,4,6-trinitrobenzene from 1,3,5-trimethoxybenzene are shown below:

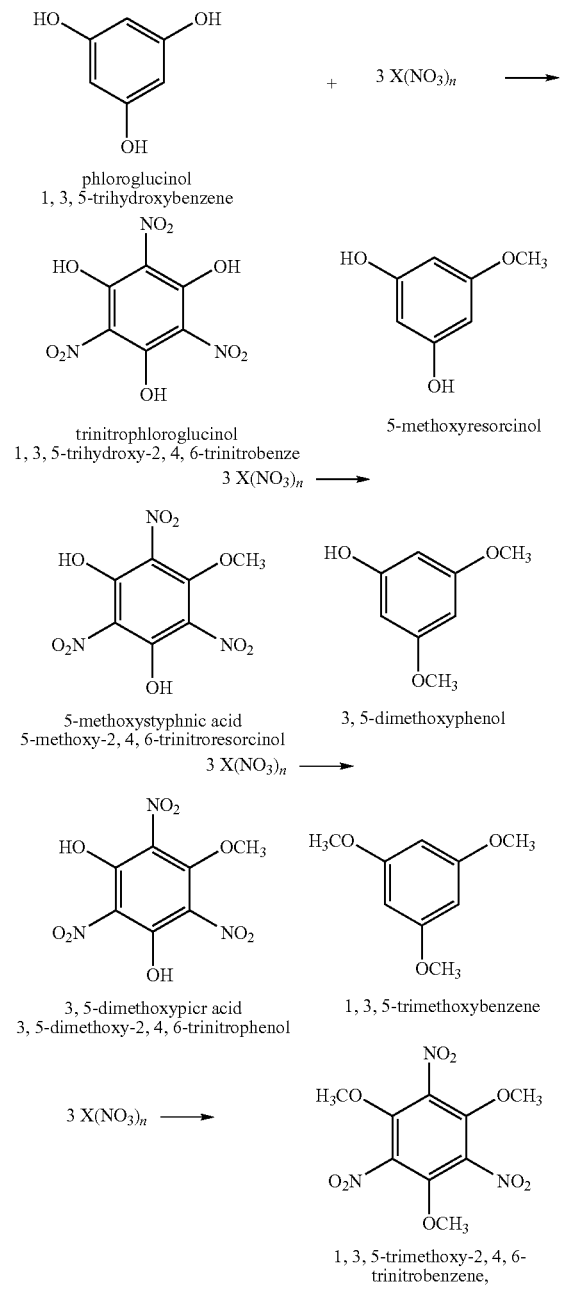

where X is Na+, K+, or NH4+. In addition, mixtures of nitrate salts may be used. While the reaction scheme above illustrates that three molar equivalents of the nitrate salt may be used relative to the nitratable aromatic compound, one or two molar equivalents of the nitrate salt may be used to produce a mono- or di-nitrated aromatic compound.

The nitratable aromatic compound may be nitrated using a mixture of the at least one nitrate salt and sulfuric acid. Water may, optionally, be present in the nitrate salt/sulfuric acid mixture. To nitrate the nitratable aromatic compound, a sulfuric acid solution may be added to a reaction vessel and may be cooled to a temperature within a range of from about 0° C. to about 10° C. The reaction vessel is compatible with the conditions of the nitration reaction, and may be a round-bottom flask or a reactor. For the sake of example only, when commercial quantities of the nitrated aromatic compound are to be produced, the reaction vessel may be a 5-, 50-, or 500-gallon Pfaudler type glass-lined reactor. In one embodiment, the sulfuric acid solution is cooled to a temperature of about 5° C. before adding the nitrate salt. The temperature of the sulfuric acid solution may be reduced using a cooling source, such as an ice water bath, to cool the reaction vessel. The sulfuric acid solution may include between about 80% by weight (wt %) and about 100 wt % sulfuric acid and between about 0 wt % and about 20 wt % water. Particularly, the sulfuric acid solution may include between about 90 wt % and about 100 wt % sulfuric acid and between about 0 wt % and about 10 wt % water. In one embodiment, the sulfuric acid solution includes about 96 wt % sulfuric acid and about 4 wt % water, which is known in the art as "concentrated sulfuric acid." The concentrated sulfuric acid may react violently with water if mixed quickly and, thus, may be handled in a fume hood.

After cooling, the nitrate salt may be slowly added to, and combined with, the sulfuric acid solution in the reaction vessel to form the nitrate salt/sulfuric acid mixture. A stoichiometric equivalent of the nitrate salt may be dissolved in the sulfuric acid solution. Depending on the desired degree of nitration of the nitrated aromatic compound, the amount of nitrate salt added to the reaction vessel may be a molar equivalent or greater, relative to the nitratable aromatic compound. If a nitrated aromatic compound having one nitro group is to be produced, one mole of the nitrate salt may be added to the reaction vessel per mole of the nitratable aromatic compound. If two or three nitro groups are to be present on the nitrated aromatic compound, two moles or three moles, respectively, of the nitrate salt may be added to the reaction vessel per mole of the nitratable aromatic compound. The nitrate salt/sulfuric acid mixture may be a solution or a suspension. The nitrate salt may be added to the sulfuric acid solution while stirring at a rate such that the temperature of the sulfuric acid solution does not exceed about 30° C., and, more particularly, about 10° C. To maintain the sulfuric acid solution at this temperature, the reaction vessel may be continuously cooled during addition of the nitrate salt while stirring. Combining the nitrate salt with the sulfuric acid solution produces a lower exotherm compared to the exotherm produced during conventional techniques of nitrating aromatics, such as when nitric acid and sulfuric acid are combined. The nitratable aromatic compound may be added to the nitrate salt/sulfuric acid mixture to form a reaction mixture. The aromatic compound may be added to the reaction mixture, for example, stepwise, continuously or in a single portion. The temperature of the nitrate salt/sulfuric acid mixture may, optionally, be reduced to less than or equal to about 5° C. before adding the nitratable aromatic compound. Substantially all of the sulfuric acid and nitrate salt may be present in the reaction vessel before adding the nitratable aromatic compound.

After adding the nitratable aromatic compound, the cooling source may be removed and the temperature of the reaction mixture may increase. Once the cooling source is removed, the temperature of the reaction mixture may increase due to the exothermic nature of the nitration reaction. Optionally, the reaction mixture may be heated to a temperature in a range of from about 0° C. to about 27° C. and, more particularly, about 25° C. In some embodiments, after the reaction mixture has increased to ambient temperature (i.e., between about 23° C. and about 27° C.), the temperature of the reaction mixture may be increased to between about 30°

C. and about 70° C. and, more particularly, about 55° C. Upon addition of the nitratable aromatic compound to the nitrate salt/sulfuric acid mixture, the nitratable aromatic compound may become directly nitrated, producing the nitrated aromatic compound.

Once the cooling source is removed, the reaction mixture may, optionally, be stirred for from about 1 minute to about 30 minutes to produce a mixture of the nitrated aromatic compound and byproducts or contaminants. Continuous stirring may facilitate the nitration reaction by providing adequate mixing of the reactants. In one embodiment, the reaction mixture is stirred for about 10 minutes. The nitrated aromatic compound may then be precipitated by cooling the reaction mixture to a temperature of from about 0° C to about 25° C. The slurry or solution may be cooled, for example, by adding it to crushed ice, or ice water, or a mixture thereof and stirring for about 10 minutes to about 60 minutes or until substantially all of the ice has melted.

Once cooled, the heterogeneous mixture may be filtered and washed to isolate the nitrated aromatic compound. The heterogeneous mixture may be discharged onto a filter, such as a Buchner type funnel or an indexing vacuum belt filter ("IVBF"), and washed with a volume of distilled water or an aqueous, acidic solution to remove the byproducts or contaminants. The aqueous, acidic solution may include from about 0.5 wt % to about 25 wt % of an acid, such as hydrochloric acid (HCl), nitric acid, sulfuric acid, or hydrogen bromide. In one embodiment, the acid is HCl having a temperature of from about 0° C. to about room temperature. The nitrated aromatic compound has a low solubility in the aqueous, acidic solution, enabling the nitrated aromatic compound to precipitate from the reaction mixture after it is added to the crushed ice, or ice water. The resulting acid-wet nitrated aromatic compound may be substantially free of the byproducts or contaminants and is dried under a reduced pressure. By way of non-limiting example, the nitrated aromatic compound may be dried under a pressure of less than about atmospheric pressure (i.e., about 101.325 kPa). The yield of the nitrated aromatic compound may be from about 50% to about 95%, and the purity of the nitrated aromatic compound may be from about 95% to about 99%. The nitrated aromatic compound may be a mono-, di-, or tri-nitrated compound depending on the amount of nitrate salt used in the nitration reaction. The nitrated aromatic compound may include, but is not limited to, trinitrophloroglucinol, 5-methoxystyphnic acid, 3,5-dimethoxypicric acid, or 1,3,5-trimethoxy-2,4,6-trinitrobenzene.

By using a combination of a nitrate salt and sulfuric acid for the nitration reaction, the reaction times, reaction temperatures and the amount of starting materials for the nitration reaction are reduced compared to conventional techniques. Nitrating aromatic compounds using the nitrate salt and sulfuric acid provides complete nitration in about 1 hour or less at a temperature of about 25° C. In addition, the nitration reaction produces fewer undesirable byproducts and uses starting materials having increased stability, reduced toxicity and reduced cost. Specifically, the nitrate salts have a substantially increased stability in comparison to reagents, such as nitric acid, which are used in conventional nitration processes. The nitrate salts are also more economical, have a longer shelf life, and are less hazardous than the mixture of acids (nitric acid and sulfuric acid) currently used in the art to nitrate phloroglucinol. Furthermore, the nitrate salts are much easier to handle and enable the reaction to take place in substantially increased anhydrous conditions, if desirable. The present method of nitrating the aromatic compounds also reduces or eliminates the production of nitrogen oxides ($NO_x$) that are formed using conventional nitration processes. In addition, the sulfuric acid is partially neutralized by the nitrate salt during the nitration reaction, reducing the amount of spent sulfuric acid to be disposed of.

The nitrated aromatic compounds produced by the direct nitration reaction may be used as reagents for producing energetic materials, such as TATB. By way of non-limiting example, the nitrated aromatic compounds described above may be converted to TATB using an alkylation reaction, followed by an amination reaction, as described in co-pending U.S. patent application Ser. No. 11/744,986 entitled "METHODS OF PRODUCING 1,3,5-TRIAMINO-2,4,6-TRINITROBENZENE," filed May 7, 2007, and assigned to the Assignee of the present application, and in co-pending U.S. patent application Ser. Nos. 12/484,985 entitled "METHODS OF PRODUCING 1,3,5-TRIAMINO-2,4,6-TRINITROBENZENE," and 12/484,917 entitled "METHODS FOR THE PRODUCTION OF 1,3,5-TRIAMINO-2,4,6-TRINITROBENZENE," each of which was filed on Jun. 15, 2009, and assigned to the Assignee of the present application. The disclosure of each of the three above-mentioned applications is incorporated by reference herein in its entirety. By way of non-limiting example, if trinitrophloroglucinol, 5-methoxystyphnic acid, or 3,5-dimethoxypicric acid is produced by the direct nitration reaction, each of these compounds may be alkylated and subsequently aminated to produce TATB. If 1,3,5-trimethoxy-2,4,6-trinitrobenzene is produced by the direct nitration reaction, this compound may be aminated to produce TATB. Since each of 5-methoxystyphnic acid, 3,5-dimethoxypicric acid, and 1,3,5-trimethoxy-2,4,6-trinitrobenzene includes at least one methoxy group, the amount of alkylating agent used to alkylate the nitrated aromatic compounds may be reduced compared to the amount of alkylating agent used in conventional techniques. The nitration process may further substantially reduce reaction time and reaction temperature in comparison to conventional nitration processes.

The following examples serve to explain embodiments of the present invention in more detail. These examples are not to be construed as being exhaustive or exclusive as to the scope of this invention.

EXAMPLES

Example 1

Synthesis of Trinitrophloroglucinol Monohydrate from Phloroglucinol Dihydrate (PGDH)

Sulfuric acid (30 mL (96%)) was placed in a 250-ml round-bottom flask equipped with a cooling bath and a magnetic stirrer and the round-bottom flask was cooled to about 5° C. Ammonium nitrate (1.48 g (18.48 mmol)) was added to the round-bottom flask at a rate such that the temperature did not exceed about 10° C. The temperature of the round-bottom flask was again reduced to about 5° C. and PGDH (1.00 g (6.16 mmol)) was added thereto. The PGDH was added to the round-bottom flask at a rate such that the temperature did not exceed about 15° C. After addition of the PGDH, the cooling bath was removed and the mixture was stirred for about 10 minutes. The heterogeneous reaction mixture was added in a single portion to crushed ice (about 100 g) and was gently stirred until the ice had substantially melted, yielding a yellow solid. The solid was isolated by filtration and washed with a 10% HCl solution. The solid was air dried under reduced pressure (i.e., less than about atmospheric pressure), yielding 1.57 g (91% yield based on PGDH) of trinitrophloroglucinol monohydrate. FIG. 1 shows a proton nuclear magnetic resonance ($^1$H NMR) spectrum consistent with trinitrophloroglucinol monohydrate.

Example 2

Synthesis of 5-Methoxystyphnic Acid from 5-Methoxyresorcinol (5-MR)

Figure 2:
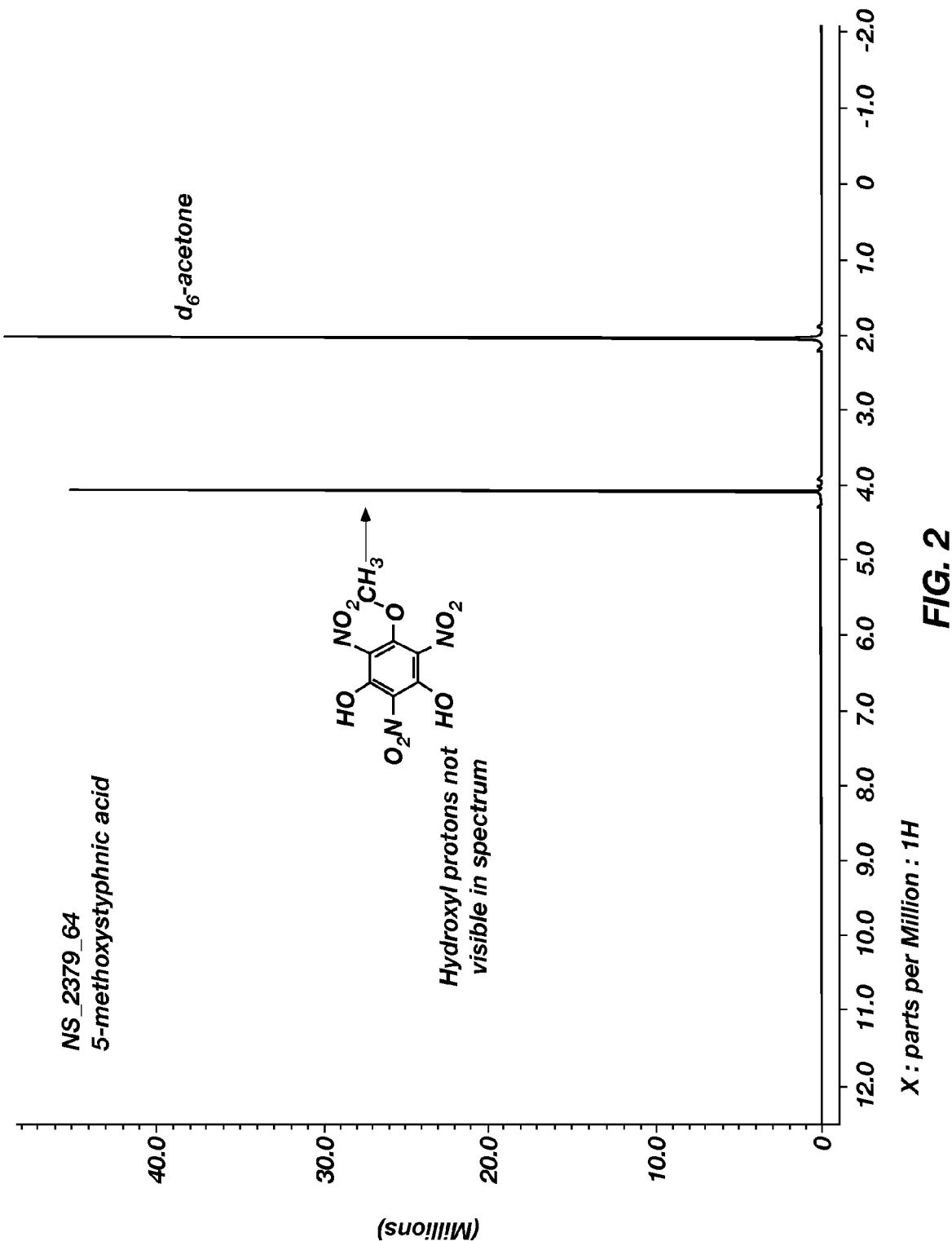

Sulfuric acid (30 mL (96%)) was placed in a 250-ml round-bottom flask equipped with a cooling bath and a magnetic stirrer and the round-bottom flask was cooled to about 5° C. Ammonium nitrate (1.72 g (21.48 mmol)) was added to the round-bottom flask at a rate such that the temperature did not exceed about 10° C. The temperature of the round-bottom flask was reduced to about 5° C. and 5-MR (1.00 g (7.12 mmol)) was added thereto. The 5-MR was added to the round-bottom flask at a rate such that the temperature did not exceed about 15° C. After addition of the 5-MR, the cooling bath was removed, and the reaction mixture was stirred for about 10 minutes. The reaction mixture was added in a single portion to crushed ice (about 200 g) and was gently stirred until the ice had substantially melted, yielding a yellowish solid. The solid was isolated by filtration and washed with a 10% HCl solution. The solid was air dried under reduced pressure (i.e., less than about atmospheric pressure), yielding 1.89 g (96% yield based on 5-MR) of 5-methoxystyphnic acid. FIG. 2 shows a $^1$H NMR spectrum consistent with 5-methoxystyphnic acid.

Example 3

Synthesis of 3,5-Dimethoxypicric Acid from 3,5-Dimethoxyphenol (3,5-DMP)

Figure 3:
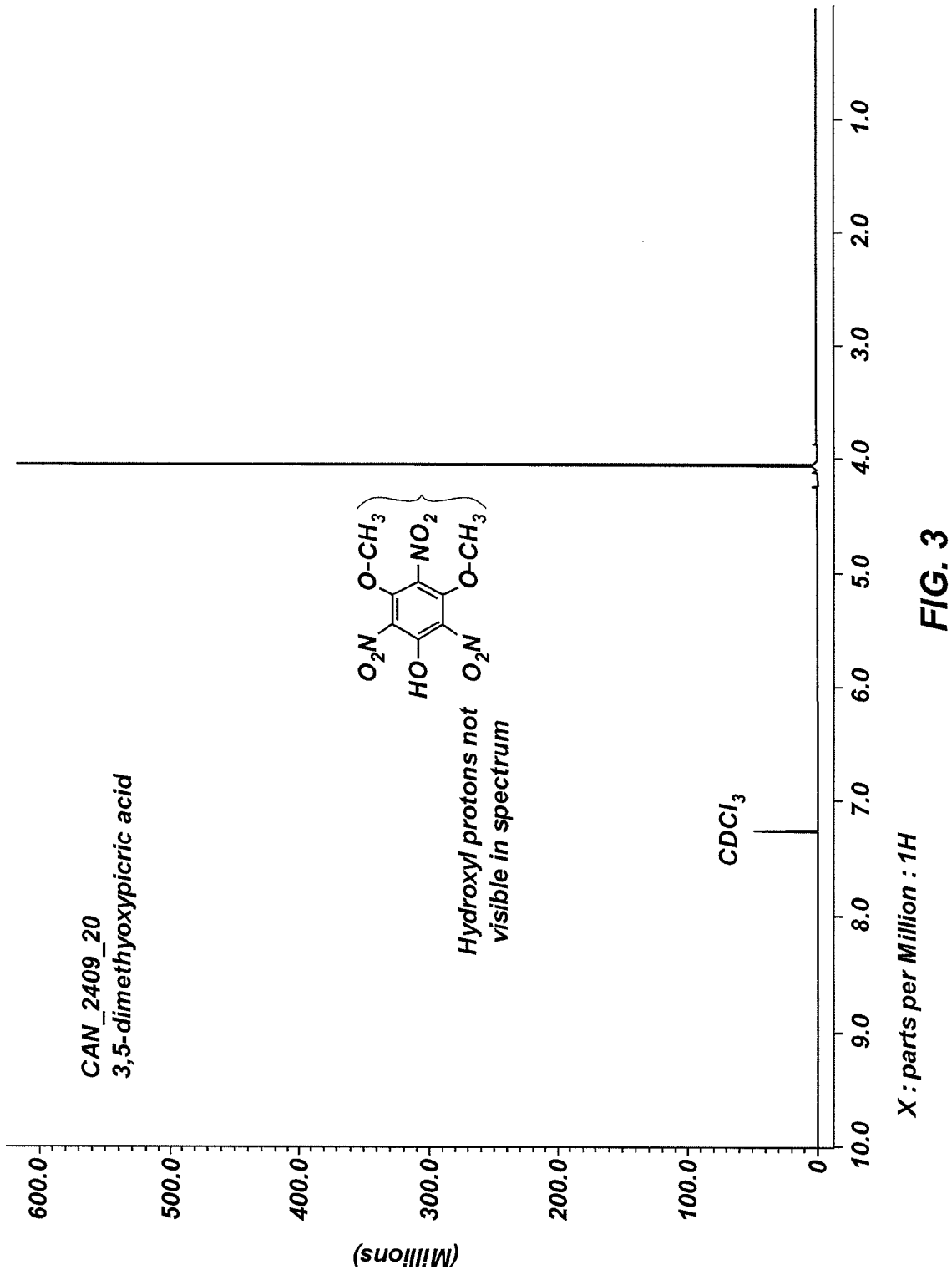

Sulfuric acid (10 mL (96%)) was placed in a 25-ml round-bottom flask equipped with a cooling bath and a magnetic stirrer and the round-bottom flask was cooled to about 5° C. Ammonium nitrate (0.39 g (4.87 mmol)) was added with stirring to the round-bottom flask at a rate such that the temperature did not exceed about 10° C. The temperature of the round-bottom flask was reduced to about 5° C. and 3,5-DMP (0.25 g (1.62 mmol)) was added thereto. The 3,5-DMP was added to the round-bottom flask at a rate such that the temperature did not exceed about 15° C. After addition of the 3,5-DMP, the cooling bath was removed, and the reaction mixture was stirred for about 10 minutes. The reaction mixture was added in a single portion to crushed ice (about 150 g) and was gently stirred until the ice had substantially melted, resulting in precipitation of a yellowish solid. The solid was isolated by filtration and washed with a 10% HCl solution. The solid was air dried under reduced pressure (i.e., less than about atmospheric pressure), yielding 1.89 g (96% yield based on 3,5-DMP) of 3,5-dimethoxypicric acid. FIG. 3 shows a $^1$H NMR spectrum consistent with 3,5-dimethoxypicric acid.

Example 4

Synthesis of 1,3,5-Trimethoxy-2,4,6-Trinitrobenzene from 1,3,5-Trimethoxybenzene (1,3,5-TMB)

Figure 4:
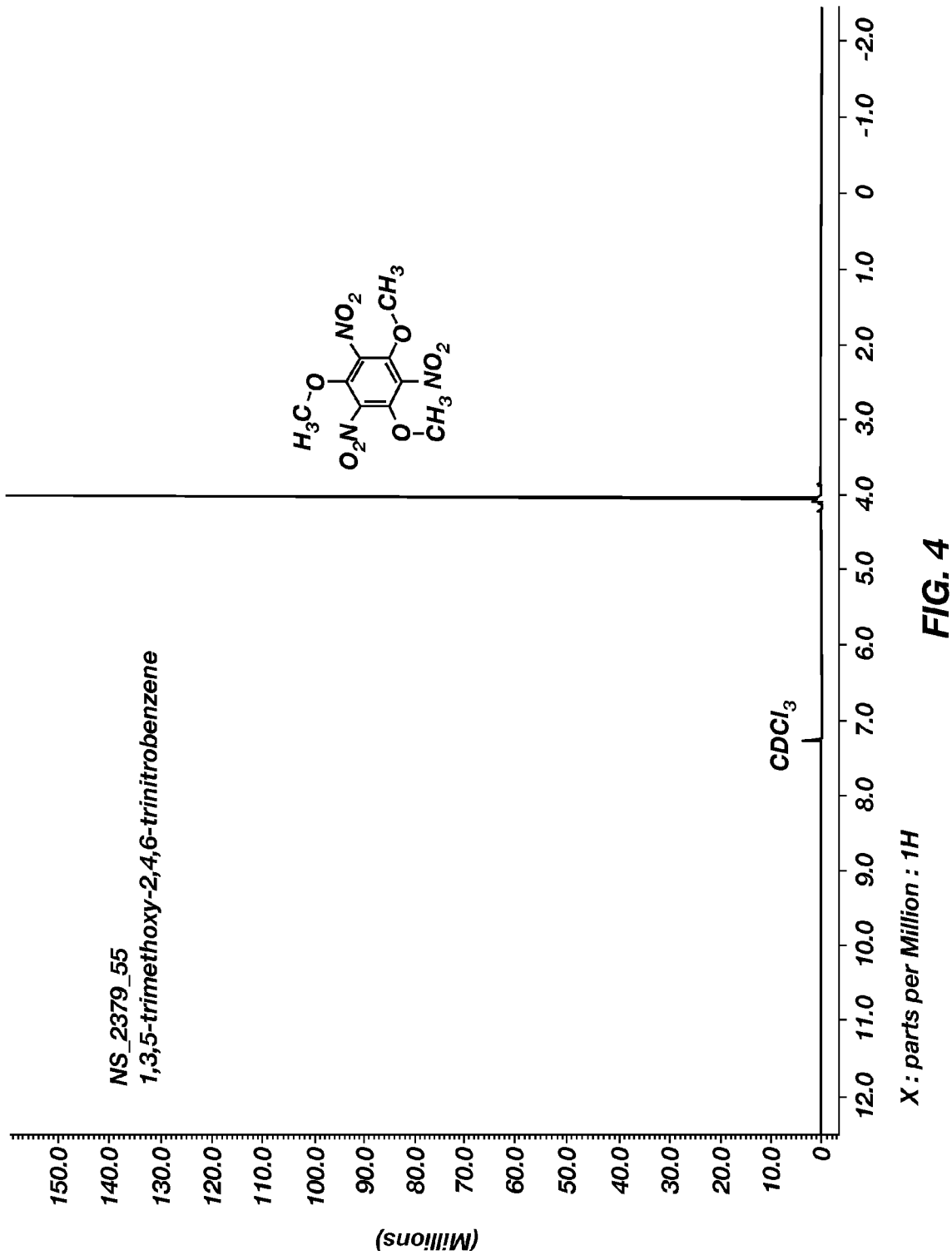

Sulfuric acid (10 mL (96%)) was placed in a 25-ml round-bottom flask equipped with a cooling bath and a magnetic stirrer and the round-bottom flask was cooled to about 5° C. Ammonium nitrate (0.36 g (4.50 mmol)) was added with stirring to the round-bottom flask at a rate such that the temperature did not exceed about 10° C. The temperature of the round-bottom flask was reduced to about 5° C. and 1,3,5-TMB (0.25 g (1.49 mmol)) was added thereto. The 1,3,5-TMB was added to the round-bottom flask at a rate such that the temperature did not exceed about 15° C. Vigorous stirring was maintained to prevent concentrating the 1,3,5-TMB in the center of the round-bottom flask. After addition of the 1,3,5-TMB was complete the temperature of the round-bottom flask was increased to about 55° C. Once at 55° C. the solution was added in a single portion to crushed ice (about 100 g). The mixture was stirred gently until the ice had substantially melted, resulting in precipitation of a yellowish solid. The solid was filtered and washed with distilled water and was air dried under reduced pressure (i.e., less than about atmospheric pressure), yielding 0.27 g (60% yield based on 1,3,5-trimethoxybenzene) of 1,3,5-trimethoxy-2,4,6-trinitrobenzene. FIG. 4 shows a $^1$H NMR spectrum consistent with 1,3,5-trimethoxy-2,4,6-trinitrobenzene.

Example 5

Synthesis of Trinitrophloroglucinol Monohydrate from Phloroglucinol Dihydrate (PGDH)

Concentrated sulfuric acid is placed in a round-bottom flask equipped with a cooling bath and a magnetic stirrer and the round-bottom flask is cooled to about 5° C. Potassium nitrate (about three molar equivalents with respect to PGDH) is added to the round-bottom flask at a rate such that the temperature does not exceed about 10° C. The temperature of the round-bottom flask is again reduced to about 5° C. and PGDH is added thereto. The PGDH is added to the round-bottom flask at a rate such that the temperature does not exceed about 15° C. After addition of the PGDH, the cooling bath is removed and the reaction mixture is stirred for about 10 minutes. The reaction mixture is added in a single portion to crushed ice (about 100 g) and is gently stirred until the ice substantially melts, yielding a yellowish solid. The solid is isolated by filtration and washed with a 10% HCl solution. The solid is air dried under pressure (i.e., less than about atmospheric pressure), and yields trinitrophloroglucinol monohydrate.

Example 6

Synthesis of 1,3,5-Trimethoxy-2,4,6-Trinitrobenzene from 1,3,5-Trimethoxybenzene (1,3,5-TMB)

Sulfuric acid is placed in a round-bottom flask equipped with a cooling bath and a magnetic stirrer and the round-bottom flask is cooled to about 5° C. Sodium nitrate (about three molar equivalents with respect to 1,3,5-TMB) is added with stirring to the round-bottom flask at a rate such that the temperature does not exceed about 10° C. The temperature of the round-bottom flask is reduced to about 5° C. and 1,3,5-TMB is added thereto. The 1,3,5-TMB is added to the round-bottom flask at a rate such that the temperature does not exceed about 15° C. Vigorous stirring is maintained to prevent concentrating the 1,3,5-TMB in the center of the round-bottom flask. After addition of the 1,3,5-TMB is complete the temperature of the round-bottom flask is increased to about 55° C. Once at 55° C. the solution is added in a single portion to crushed ice (about 100 g). The mixture is stirred vigorously until the ice substantially melts, resulting in precipitation of a yellowish solid. The solid is isolated by filtration, washed with distilled water and is air dried under reduced pressure (i.e., less than about atmospheric pressure), yielding 1,3,5-trimethoxy-2,4,6-trinitrobenzene.

Example 7

Synthesis of Trinitrophloroglucinol Monohydrate from Phloroglucinol Dihydrate (PGDH)

Sulfuric acid is placed in a round-bottom flask equipped with a cooling bath and a magnetic stirrer and the round-bottom flask is cooled to about 5° C. Potassium nitrate (about three molar equivalents with respect to PGDH) is added with stirring to the round-bottom flask at a rate such that the temperature does not exceed about 10° C. The temperature of the round-bottom flask is reduced to about 5° C. and PGDH is added thereto. The PGDH is added to the round-bottom flask at a rate such that the temperature does not exceed about 15° C. After addition of the PGDH, the cooling bath is removed and the reaction mixture is stirred for about 10 minutes. The reaction mixture is added in a single portion to crushed ice and gently stirred until the ice has substantially melted, yielding a yellowish solid. The solid is isolated by filtration, washed with a 10% HCl solution, and air dried under reduced pressure (i.e., less than about atmospheric pressure), yielding trinitrophloroglucinol monohydrate.

While the invention may be susceptible to implementation with various modifications and in various forms, specific embodiments have been described in detail herein. However, it should be understood that the invention is not intended to be limited to the particular forms disclosed. Rather, the invention is to cover all modifications, equivalents, and alternatives falling within the scope of the invention as defined by the following appended claims.

What is claimed is:

1. A method of nitrating a compound, comprising:
   combining at least one nitrate salt and a sulfuric acid solution to form a reaction mixture; and
   exposing phloroglucinol or a methoxy derivative thereof to the reaction mixture to nitrate the phloroglucinol or methoxy derivative thereof.

2. The method of claim 1, wherein combining at least one nitrate salt and a sulfuric acid solution to form a reaction mixture comprises combining the at least one nitrate salt and the sulfuric acid solution comprising from approximately 90% by weight to approximately 100% by weight of sulfuric acid to form the reaction mixture.

3. The method of claim 1, wherein combining at least one nitrate salt and a sulfuric acid solution to form a reaction mixture comprises combining the at least one nitrate salt and the sulfuric acid solution comprising 96% by weight sulfuric acid and 4% by weight water to form the reaction mixture.

4. The method of claim 1, wherein combining at least one nitrate salt and a sulfuric acid solution to form a reaction mixture comprises combining at least one of sodium nitrate, potassium nitrate, ammonium nitrate, calcium nitrate, and magnesium nitrate with the sulfuric acid solution.

5. The method of claim 1, wherein combining at least one nitrate salt and a sulfuric acid solution to form a reaction mixture comprises adding the at least one nitrate salt into the sulfuric acid solution at a temperature in a range of from about 0° C. to about 30° C. to form the reaction mixture.

6. The method of claim 1, wherein combining at least one nitrate salt and a sulfuric acid solution to form a reaction mixture comprises adding the at least one nitrate salt into the sulfuric acid solution at a rate sufficient to maintain a temperature of the reaction mixture at less than about 10° C.

7. The method of claim 1, wherein exposing phloroglucinol or a methoxy derivative thereof to the reaction mixture comprises exposing at least one of phloroglucinol, 5-methoxyresorcinol, 3,5-dimethoxyphenol, and 1,3,5-trimethoxybenzene to the reaction mixture.

8. The method of claim 1, wherein exposing phloroglucinol or a methoxy derivative thereof to the reaction mixture comprises increasing a temperature of the phloroglucinol or the methoxy derivative thereof and the reaction mixture to a temperature within a range of from about 0° C. to about 27° C.

9. The method of claim 1, wherein combining at least one nitrate salt and a sulfuric acid solution and exposing phloroglucinol or a methoxy derivative thereof to the reaction mixture comprises combining the at least one nitrate salt and the sulfuric acid solution and exposing the phloroglucinol or the methoxy derivative thereof in a single reaction vessel.

10. The method of claim 1, wherein exposing phloroglucinol or a methoxy derivative thereof to the reaction mixture comprises mixing the phloroglucinol or the methoxy derivative thereof with the reaction mixture for from about 5 minutes to about 15 minutes.

11. A method of nitrating a compound, comprising:
    reacting phloroglucinol or a methoxy derivative thereof with a reaction mixture comprising sulfuric acid and at least one nitrate salt to nitrate the phloroglucinol or the methoxy derivative thereof.

12. The method of claim 11, wherein reacting phloroglucinol or a methoxy derivative thereof with a reaction mixture comprising sulfuric acid and at least one nitrate salt comprises reacting three molar equivalents of the at least one nitrate salt with the phloroglucinol or the methoxy derivative thereof.

13. The method of claim 11, wherein reacting phloroglucinol or a methoxy derivative thereof with a reaction mixture comprising sulfuric acid and at least one nitrate salt comprises producing a mononitrated, dinitrated, or trinitrated reaction product of phloroglucinol or the methoxy derivative thereof.

14. The method of claim 11, wherein reacting phloroglucinol or a methoxy derivative thereof with a reaction mixture comprising sulfuric acid and at least one nitrate salt comprises producing trinitrophloroglucinol, 5-methoxystyphnic acid, 3,5-dimethoxypicric acid, or 1,3,5-trimethoxy-2,4,6-trinitrobenzene.

15. The method of claim 11, wherein reacting phloroglucinol or a methoxy derivative thereof with a reaction mixture comprising sulfuric acid and at least one nitrate salt comprises adding the at least one nitrate salt to the sulfuric acid at a temperature in a range of from about 0° C. to about 15° C.

16. The method of claim 15, wherein reacting phloroglucinol or a methoxy derivative thereof with a reaction mixture comprising sulfuric acid and at least one nitrate salt comprises increasing the temperature of the phloroglucinol or the methoxy derivative thereof and the reaction mixture to a temperature of about 50° C.

17. The method of claim 11, wherein reacting phloroglucinol or a methoxy derivative thereof with a reaction mixture comprising sulfuric acid and at least one nitrate salt comprises:
    adding the at least one nitrate salt to the sulfuric acid at a temperature in a range of from about 0° C. to about 15° C.;
    mixing the phloroglucinol or the methoxy derivative thereof with the reaction mixture at a temperature in a range of from about 0° C. to about 15° C. to form a solution or slurry; and
    stirring the solution or slurry at a temperature in a range of from about 10° C. to about 25° C. to nitrate the phloroglucinol or the methoxy derivative thereof.

* * * * *

UNITED STATES PATENT AND TRADEMARK OFFICE
CERTIFICATE OF CORRECTION

PATENT NO. : 7,737,308 B1  
APPLICATION NO. : 12/484960  
DATED : June 15, 2010  
INVENTOR(S) : Nicholas A. Straessler Page 1 of 1

It is certified that error appears in the above-identified patent and that said Letters Patent is hereby corrected as shown below:

In the specification:

COLUMN 5, LINE 45, change "OH" to --OCH$_3$--  
COLUMN 5, LINE 46, change "3,5-dimethoxypicr acid" to --3,5-dimethoxypicric acid--

Signed and Sealed this  
Eighth Day of November, 2011

David J. Kappos  
*Director of the United States Patent and Trademark Office*